(12) United States Patent
Chatterjee

(10) Patent No.: US 11,963,761 B2
(45) Date of Patent: Apr. 23, 2024

(54) MEDIATION OF IN VIVO ANALYTE SIGNAL DEGRADATION

(71) Applicant: Senseonics, Incorporated, Germantown, MD (US)

(72) Inventor: Joon Chatterjee, Germantown, MD (US)

(73) Assignee: Senseonics, Incorporated, Germantown, MD (US)

(*) Notice: Subject to any disclaimer, the term of this patent is extended or adjusted under 35 U.S.C. 154(b) by 397 days.

(21) Appl. No.: 16/875,424

(22) Filed: May 15, 2020

(65) Prior Publication Data

US 2020/0359943 A1 Nov. 19, 2020

Related U.S. Application Data

(60) Provisional application No. 62/848,835, filed on May 16, 2019.

(51) Int. Cl.
| | |
|---|---|
| *A61B 5/145* | (2006.01) |
| *A61B 5/00* | (2006.01) |
| *A61B 5/1459* | (2006.01) |
| *A61B 5/1473* | (2006.01) |
| *A61B 5/1486* | (2006.01) |
| *A61L 31/04* | (2006.01) |
| *A61L 31/14* | (2006.01) |
| *A61L 31/16* | (2006.01) |
| *C08F 283/06* | (2006.01) |
| *C08K 5/55* | (2006.01) |
| *G01N 21/75* | (2006.01) |
| *G01N 21/77* | (2006.01) |
| *G01N 33/50* | (2006.01) |

(52) U.S. Cl.
CPC ...... *A61B 5/14503* (2013.01); *A61B 5/14546* (2013.01); *A61L 31/041* (2013.01); *A61L 31/145* (2013.01); *A61L 31/16* (2013.01); *C08F 283/06* (2013.01); *C08K 5/55* (2013.01); *G01N 21/75* (2013.01); *G01N 21/77* (2013.01); *G01N 33/50* (2013.01); *A61B 5/0031* (2013.01); *A61B 5/14532* (2013.01); *A61B 5/14542* (2013.01); *A61B 5/1459* (2013.01); *A61B 5/14735* (2013.01); *A61B 5/14865* (2013.01)

(58) Field of Classification Search
CPC ....... A61L 31/145; G01N 21/77; G01N 33/50
See application file for complete search history.

(56) References Cited

U.S. PATENT DOCUMENTS

| | | | |
|---|---|---|---|
| 5,512,246 A | 4/1996 | Russell et al. | |
| 5,517,313 A | 5/1996 | Colvin, Jr. | |
| 5,837,202 A * | 11/1998 | Arnold | G01N 31/221 562/444 |
| 9,414,775 B2 | 8/2016 | Colvin, Jr. et al. | |
| 9,427,181 B2 | 8/2016 | Emken et al. | |
| 9,681,824 B2 | 6/2017 | Colvin, Jr. et al. | |
| 9,693,714 B2 | 7/2017 | DeHennis et al. | |
| 9,931,068 B2 | 4/2018 | Huffstetler et al. | |
| 2002/0042065 A1* | 4/2002 | Han | A61B 5/14532 435/7.9 |
| 2010/0226961 A1* | 9/2010 | Lamberti | A61L 27/46 424/488 |
| 2011/0236989 A1* | 9/2011 | Suri | G01N 21/6428 436/172 |
| 2012/0009566 A1* | 1/2012 | Soukka | G01N 33/542 435/6.12 |
| 2012/0330120 A1* | 12/2012 | Ouyang | A61B 5/14532 600/347 |
| 2013/0161190 A1* | 6/2013 | Ewart | B01L 3/502715 204/403.03 |
| 2013/0241745 A1 | 9/2013 | Colvin, Jr. et al. | |
| 2016/0305964 A1* | 10/2016 | Gee | C07D 209/14 |

OTHER PUBLICATIONS

Lin (Clemson University TigerPrints dissertations, Aug. 2007, https://tigerprints.clemson.edu/cgi/viewcontent.cgi?article=1110&context=all_dissertations) (Year: 2007).*

* cited by examiner

*Primary Examiner* — Mark V Stevens
(74) *Attorney, Agent, or Firm* — Rothwell, Figg, Ernst & Manbeck, P.C.

(57) ABSTRACT

A sensor (e.g., an optical sensor) that may be implanted within a living animal (e.g., a human) and may be used to measure an analyte (e.g., glucose or oxygen) in a medium (e.g., interstitial fluid, blood, or intraperitoneal fluid) within the animal. The sensor may include a sensor housing, an analyte indicator covering at least a portion of the sensor housing, and one or more compounds having metal chelating moieties that reduce degradation of the analyte indicator.

28 Claims, 4 Drawing Sheets

MEDIATION OF IN VIVO ANALYTE SIGNAL DEGRADATION

CROSS-REFERENCE TO RELATED APPLICATION

The present application claims the benefit of priority to U.S. Provisional Application Ser. No. 62/848,835, filed on May 16, 2019, which is incorporated herein by reference in its entirety.

BACKGROUND

Field of Invention

The present invention relates generally to reduction of in vivo degradation of analyte sensor moieties when measuring an analyte in a medium of a living animal using a system including a sensor implanted (partially or fully) or inserted into the living animal. Specifically, the present invention relates to a sensor that utilizes one or more additives, which may be incorporated within an analyte indicator, a material covering at least a portion of the analyte indicator, and/or a material covering at least a portion of a sensor housing.

Discussion of the Background

A sensor may be implanted (partially or fully) within a living animal (e.g., a human) and used to measure an analyte (e.g., glucose, oxygen, cardiac markers, low-density lipoprotein (LDL), high-density lipoprotein (HDL), or triglycerides) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entirety.

A sensor may include an analyte indicator, which may be in the form of indicator molecules embedded in a graft (i.e., layer or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the animal's immune system may begin to attack the sensor. For instance, if a sensor is implanted in a human, white blood cells may attack the sensor as a foreign body, and, in the initial immune system onslaught, neutrophils may be the primary white blood cells attacking the sensor. The defense mechanism of neutrophils includes the release of highly caustic substances known as reactive oxygen species. The reactive oxygen species include, for example, hydrogen peroxide.

Hydrogen peroxide and other reactive species such as reactive oxygen and nitrogen species may degrade the indicator molecules of an analyte indicator. For instance, in indicator molecules having a boronate group, hydrogen peroxide may degrade the indicator molecules by oxidizing the boronate group, thus disabling the ability of the indicator molecule to bind glucose.

There is presently a need in the art for improvements in reducing analyte indicator degradation. There is also a need in the art for continuous analyte sensors having increased longevity.

SUMMARY

The present invention overcomes the disadvantages of prior systems by providing, among other advantages, reduced analyte indicator degradation.

One aspect of the present invention provides a sensor that may be for implantation or insertion within a living animal and measurement of an analyte in a medium within the living animal. The sensor may include a sensor housing, an analyte indicator covering at least a portion of the sensor housing, and one or more additives that reduce deterioration of the analyte indicator.

In some embodiments, the sensor may include at least one additive-containing polymer graft, and the one or more additives may be co-polymerized with or dispersed within the additive-containing polymer graft. In some embodiments, the additive-containing polymer graft may cover at least a portion of the sensor housing. In some embodiments, the additive-containing polymer graft may be within the sensor housing.

In some embodiments, the one or more additives may be incorporated within the analyte indicator, e.g., as a co-monomer. In some embodiments, the sensor may include a material, e.g., a membrane, covering at least a portion of the analyte indicator, and the one or more additives are incorporated within the material. In some embodiments, the sensor may include one or more compounds having metal chelating moieties.

In some embodiments, the present disclosure provides a method of fabricating a sensor for measurement of an analyte in a medium within a living animal including inserting the sensor into a composition for an amount of time sufficient to effect soaking of the composition into the analyte indicator, wherein the sensor includes a sensor housing and an analyte indicator that covers at least a portion of the sensor housing, and the composition may include one or more compounds having metal chelating moieties; and removing the sensor from the composition.

In some embodiments, the present disclosure provides a method of fabricating a sensor for measurement of an analyte in a medium within a living animal including applying an analyte indicator to a sensor housing of the sensor such that the applied analyte indicator covers at least a portion of the sensor housing, wherein the analyte indicator may include one or more compounds having metal chelating moieties that reduce deterioration of the analyte indicator.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
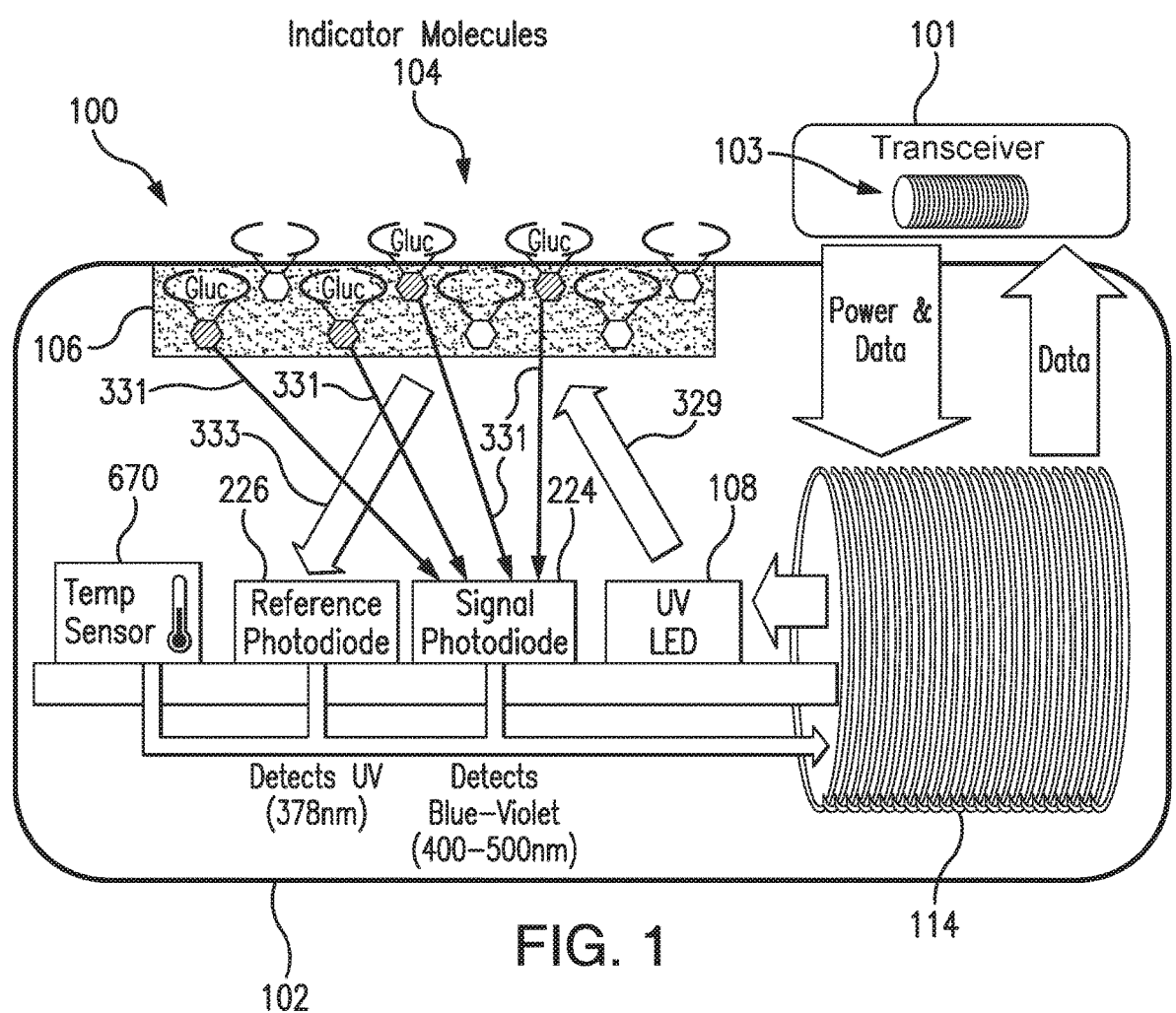
FIG. 1 is a schematic view illustrating a sensor system embodying aspects of the present invention.

FIG. 1 is a schematic view of a sensor system embodying aspects of the present invention. In some non-limiting embodiment, as shown in FIG. 1, the system may include a sensor 100 and an external transceiver 101. In some embodiments, the sensor 100 may be an implantable sensor configured to be fully or partially implanted in a living animal (e.g., a living human). The sensor 100 may be implanted, for example, in a living animal's arm, wrist, leg, abdomen, peritoneum, or other region of the living animal suitable for sensor implantation. For example, in some non-limiting embodiments, the sensor 100 may be implanted beneath the skin (i.e., in the subcutaneous or peritoneal tissues). However, this is not required, and, in some alternative embodiments, the sensor 100 may be a transcutaneous sensor.

In some embodiments, a transceiver 101 may be an electronic device that communicates with the sensor 100 to power the sensor 100, provide commands and/or data to the sensor 100, and/or receive data from the sensor 100. In some embodiments, the received data may include one or more sensor measurements. In some embodiments, the sensor measurements may include, for example and without limitation, one or more light measurements from one or more photodetectors of the sensor 100 and/or one or more temperature measurements from one or more temperature sensors of the sensor 100. In some embodiments, the transceiver 101 may calculate analyte (e.g., glucose) concentrations from the measurement information received from the sensor 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive, and the transceiver 101 may convey (e.g., periodically, such as every two minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a data from the sensor 100.

In some embodiments, as shown in FIG. 1, the transceiver 101 may include an inductive element 103, such as, for example, a coil. In some embodiments, the transceiver 101 may generate an electromagnetic wave or electrodynamic field (e.g., by using a coil) to induce a current in an inductive element 114 of the sensor 100. In some non-limiting embodiments, the sensor 100 may use the current induced in the inductive element 114 to power the sensor 100. However, this is not required, and, in some alternative embodiments, the sensor 100 may be powered by an internal power source (e.g., a battery).

In some embodiments, the transceiver 101 may convey data (e.g., commands) to the sensor 100. For example, in some non-limiting embodiments, the transceiver 101 may convey data by modulating the electromagnetic wave generated by the inductive element 103 (e.g., by modulating the current flowing through the inductive element 103 of the transceiver 101). In some embodiments, the sensor 100 may detect/extract the modulation in the electromagnetic wave generated by the transceiver 101. Moreover, the transceiver 101 may receive data (e.g., one or more sensor measurements) from the sensor 100. For example, in some non-limiting embodiments, the transceiver 101 may receive data by detecting modulations in the electromagnetic wave generated by the sensor 100, e.g., by detecting modulations in the current flowing through the inductive element 103 of the transceiver 101.

In some embodiments, as shown in FIG. 1, the sensor 100 may include a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, as shown in FIG. 1, the sensor 100 may include an analyte indicator 106. In some non-limiting embodiments, the analyte indicator 106 may be a polymer graft coated, diffused, adhered, or embedded on at least a portion of the exterior surface of the sensor housing 102. The analyte indicator 106 (e.g., polymer graft) may cover the entire surface of sensor housing 102 or only one or more portions of the surface of housing 102. As an alternative to coating the analyte indicator 106 on the outer surface of sensor housing 102, the analyte indicator 106 may be disposed on the outer surface of the sensor housing 102 in other ways, such as by deposition or adhesion. In some embodiments, the analyte indicator 106 may be a fluorescent analyte (e.g., glucose) indicating polymer. In one non-limiting embodiment, the polymer is biocompatible and stable, grafted onto the surface of sensor housing 102, designed to allow for the direct measurement of analyte in interstitial fluid (ISF), blood, or intraperitoneal fluid after implantation of the sensor 100. In some embodiments, the analyte indicator 106 may be a hydrogel.

In some embodiments, the analyte indicator 106 (e.g., polymer graft) of the sensor 100 may include indicator molecules 104. The indicator molecules 104 may be distributed throughout the entire analyte indicator 106 or only throughout one or more portions of the analyte indicator 106. The indicator molecules 104 may be fluorescent indicator molecules (e.g., TFM having the chemical name 9-[N-[6-(4,4,5,5,-tetramethyl-1,3,2-dioxaborolano)-3-(trifluoromethyl)benzyl]-N-[3-(methacrylamido)propylamino]methyl]-10-[N-[6-(4,4,5,5,-tetramethyl-1,3,2-dioxaborolano)-3-(trifluoromethyl)benzyl]-N-[2-(carboxyethyl)amino]methyl]anthracene sodium salt) or light absorbing, non-fluorescent indicator molecules. In some embodiments, the indicator molecules 104 may reversibly bind an analyte (e.g., glucose, oxygen, cardiac markers, low-density lipoprotein (LDL), high-density lipoprotein (HDL), or triglycerides). When an indicator molecule 104 has bound an analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no analyte is bound, the indicator molecule 104 may be only weakly fluorescent.

In some embodiments, the sensor 100 may include a light source 108, which may be, for example, a light emitting diode (LED) or other light source that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the sensor 100 may also include one or more photodetectors (e.g., photodiodes, phototransistors, photoresistors or other photosensitive elements). For example, in the embodiment illustrated in FIG. 1, sensor 100 has a first photodetector 224 and a second photodetector 226. However, this is not required, and, in some alternative embodiments, the sensor 100 may only include the first photodetector 224. In the case of a fluorescence-based sensor, the one or more photodetectors may be sensitive to fluorescent light emitted by the indicator molecules 104 such that a signal is generated by a photodetector (e.g., photodetector 224) in response thereto that is indicative of the level of fluorescence of the indicator molecules and, thus, the amount of analyte of interest (e.g., glucose).

Some part of the excitation light 329 emitted by the light source 108 may be reflected from the analyte indicator 106 back into the sensor 100 as reflection light 333, and some part of the absorbed excitation light may be emitted as emitted (fluoresced) light 331. In one non-limiting embodiment, the emitted light 331 may have a different wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (e.g., dichroic) filters deposited on the glass and may pass only a narrow band of wavelengths and otherwise reflect most of the received light. In some embodiments, the filters may be thin film (dichroic) filters deposited directly onto the photo detectors and may pass only a narrow band of wavelengths and otherwise reflect most of the light received thereby. The filters 112 may be identical (e.g., both filters 112 may allow signals to pass) or different (e.g., one filter 112 may be a reference filter and another filter 112 may be a signal filter).

In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the analyte indicator 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the analyte indicator 106, and, therefore, a greater number of photons striking the first photodetector 224.

In some embodiments, as shown in FIG. 1, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, U.S. application Ser. No. 13/650,016, filed on Oct. 11, 2012, U.S. Pat. No. 9,681,824 (Colvin and Jiang), and U.S. Pat. No. 9,427,181 (Emken et al.), all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

In some embodiments, the sensor 100 may include a transceiver interface device, and the transceiver 101 may include a sensor interface device. In some embodiments where the sensor 100 and transceiver 101 include an antenna or antennas (e.g., inductive elements 103 and 114), the transceiver interface device may include the inductive element 114 of the sensor 100, and the sensor interface device may include the inductive element 103 of the transceiver 101. In some of the transcutaneous embodiments where there exists a wired connection between the sensor 100 and the transceiver 101, the transceiver interface device and sensor interface device may include the wired connection.

Figure 2:
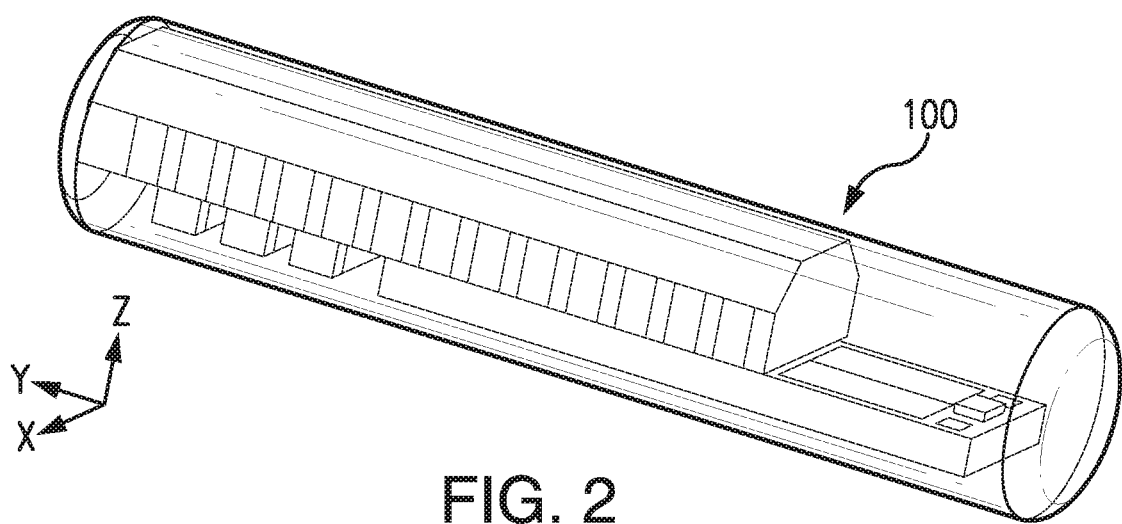
FIG. 2 illustrates a perspective view of a sensor embodying aspects of the present invention.
Figure 3:
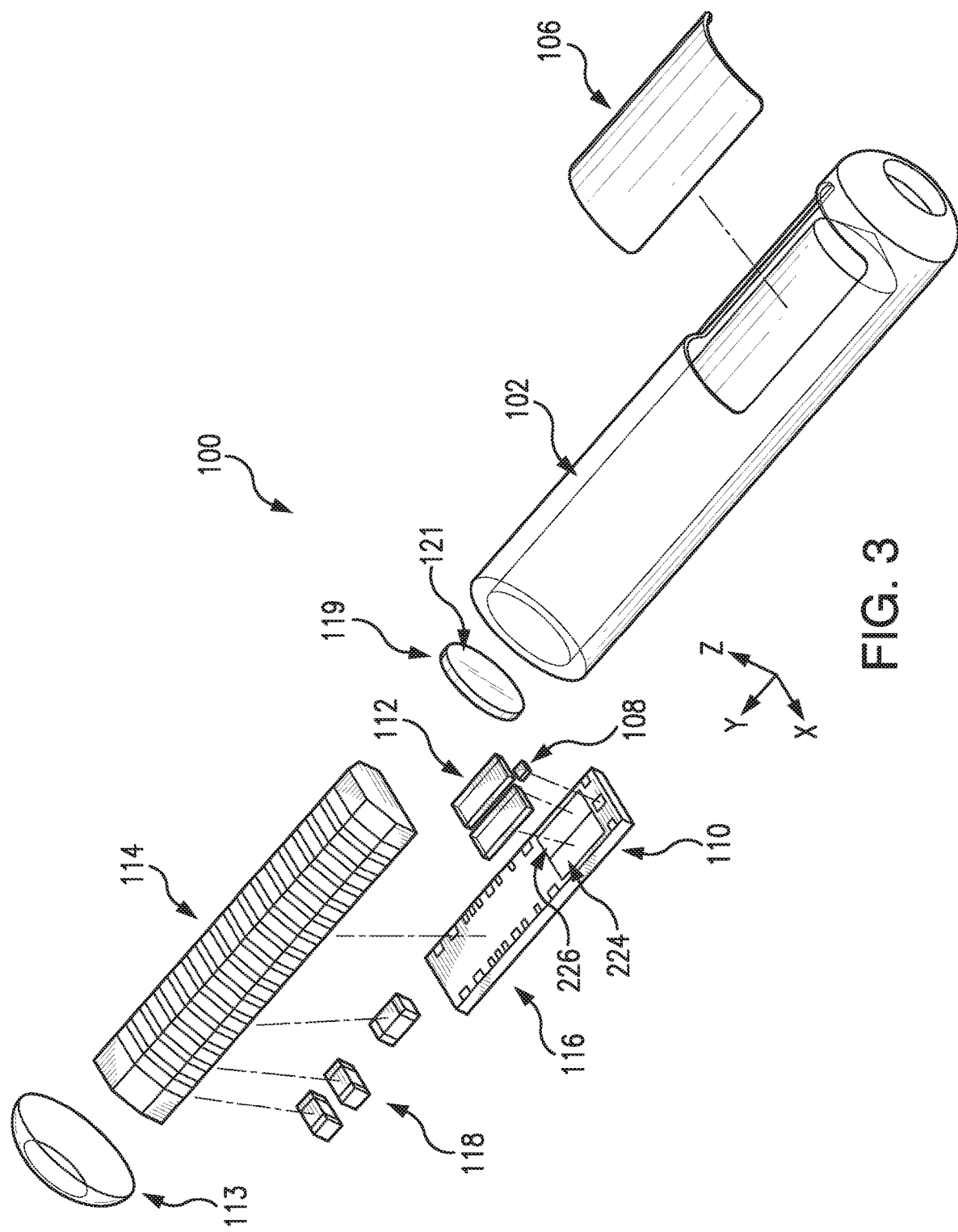
FIG. 3 illustrates an exploded view of a sensor embodying aspects of the present invention.

FIGS. 2 and 3 illustrate a non-limiting embodiment of a sensor 100 embodying aspects of the present invention that may be used in the sensor system illustrated in FIG. 1. FIGS. 2 and 3 illustrate perspective and exploded views, respectively, of the non-limiting embodiment of the sensor 100.

In some embodiments, as illustrated in FIG. 3, the sensor housing 102 may include an end cap 113. In some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, as illustrated in FIG. 3, the sensor 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from exiting the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

In some embodiments, the specific composition of the analyte indicator 106 and the indicator molecules 104 may vary depending on the particular analyte the sensor is to be used to detect and/or where the sensor is to be used to detect the analyte (e.g., in the in subcutaneous tissues, blood, or peritoneum). In some embodiments, the analyte indicator 106 facilitates exposure of the indicator molecules 104 to the analyte. In some embodiments, the indicator molecules 104 may exhibit a characteristic (e.g., emit an amount of fluorescence light) that is a function of the concentration of the specific analyte to which the indicator molecules 104 are exposed.

In some embodiments, the sensor 100 may include at least one drug eluting polymer matrix and/or a layer of catalyst and/or one or more therapeutic agents that may be provided on, incorporated in, or dispersed within the analyte indicator or sensor housing as described in U.S. Pat. No. 9,931,068 (Huffstetler et al.), which is incorporated herein by reference in its entirety. In some embodiments, the one or more therapeutic agents may be incorporated in the analyte indicator 106. In some embodiments, the sensor 100 may include a membrane covering at least a portion of the analyte indicator 106, and the one or more therapeutic agents may be incorporated within the membrane. In some embodiments, the one or more therapeutic agents include dexamethasone, triamcinolone, betamethasone, methylprednisolone, beclometasone, fludrocortisone, derivatives thereof, and analogs thereof, a glucocorticoid, an anti-inflammatory drug, e.g., a non-steroidal anti-inflammatory drug including but not limited to acetylsalicylic acid, isobutylphenylpropanoic acid.

The implantation or insertion of a medical device, such as a bio-sensor, into a user/patient's body can cause the body to exhibit adverse physiological reactions that are detrimental to the functioning of the device. The reactions may range from infections due to implantation surgery to the immunological response of a foreign object implanted in the body. That is, the performance of the implantable bio-sensor can be hindered or permanently damaged in vivo via the immunological response to an infection or the device itself. In particular, the performance of the analyte indicator 106 may be deteriorated by the immunological response of the body into which the sensor 100 is implanted. For example, as explained above, white blood cells, including neutrophils, may attack an implanted sensor 100. The neutrophils release, inter alia, hydrogen peroxide, which may degrade indicator molecules 104 (e.g., by oxidizing a boronate group of an indicator molecule 104 and disabling the ability of the indicator molecule 104 to bind glucose).

In some embodiments, the sensor 100 may include one or more additives that interact or react with one or more degradative species without compromising signal integrity or performance of the sensor device. The degradative species may include one or more of hydrogen peroxide, a reactive oxygen species, a reactive nitrogen species, a free radical, an enzyme, and a metal ion. In some embodiments, the additive may be incorporated into the analyte indicator 106, which may cover at least a portion of the sensor housing 102. In some embodiments, the additive may be copolymerized with the indicator molecules 104. In some embodiments, the one or more additives may be provided in the analyte indicator 106 (e.g., polymer graft). In some embodiments, the one or more additives may interact and/or react with degradative species. In some embodiments, the one or more additives may neutralize the degradative species. In some embodiments, the one or more additives may bind to the degradative species. In some embodiments, the one or more additives may sequester the degradative species so as to inhibit, reduce, and/or prevent degradation of the analyte indicator by the degradative species. Accordingly, in some embodiments, the one or more additives reduce deterioration of the analyte indicator 106.

In some non-limiting embodiments, the one or more additives may be metal chelating moieties that interact with degradative metal ions without compromising signal integrity or performance of the sensor.

In some non-limiting embodiments, a sensor 100 for measurement of an analyte (e.g., glucose) in a medium (e.g., interstitial fluid) within a living animal (e.g., a human) may contain one or more of the following components: a sensor housing 102; a light source 108 within the sensor housing 102 configured to emit excitation light 329; an analyte indicator 106 covering a portion of the sensor housing 102; one or more indicator molecules 104 that are part of (e.g. distributed throughout) the analyte indicator 106, reversibly bind the analyte, are positioned to be irradiated by the excitation light 329, and are configured to emit light 331 indicative of the amount of the analyte in the medium within the living animal; one or more photodetectors 224 within the sensor housing 102 that are sensitive to light 331 emitted by the one or more indicator molecules 104 and configured to generate a signal indicative of the amount of the analyte in the medium within the living animal; one or more photodetectors 226 within the sensor housing 102 that are sensitive to reflection light 333 and configured to generate a reference signal indicative of the amount of received reflection light 333; and one or more compounds having metal chelating moieties that interact with degradative species without compromising signal integrity or performance of the sensor 100. In some non-limiting embodiments, the sensor 100 may include a drug eluting matrix and/or a layer of catalyst provided on or incorporated in the analyte indicator 106 and/or sensor housing 102.

In some non-limiting embodiments, the one or more of the compounds having metal chelating moieties may contain: ethylenediaminetetraacetic acid (EDTA) and related compounds including but not limited to EDTA free acid, salts, esters, solvates, and hydrates thereof; cyclohexyl EDTA; cyclohexyl EDTA monoanhydride (CDTAMA); trans-1,2-Diaminocyclohexane-N,N,N',N'-tetraaceticacid, monohydrate (CyDTA); N,N-Bis(2-hydroxyethyl)glycine (DHEG); 1,3-Diamino-2-hydroxypropane-N,N,N',N'-tetraacetic acid (DTPA-OH); Ethylenediamine-N,N'-diacetic acid (EDDA); Ethylenediamine-N,N'-dipropionic acid dihydrochloride (EDDP); Ethylenediamine-N,N'-bis(methylenephosphonic acid), hemihydrate (EDDPO); N-(2-Hydroxyethyl)ethylenediamine-N,N',N'-triacetic acid (EDTA-OH); Ethylenediamine-N,N,N',N'-tetrakis(methylenephosponic acid) (EDTPO); O,O'-bis(2-aminoethyl)ethyleneglycol-N,N,N', N'-tetraacetic acid (EGTA); N,N-bis(2-hydroxybenzyl)ethylenediamine-N,N-diacetic acid (HBED); 1,6-Hexamethylenediamine-N,N,N',N'-tetraacetic acid (HDTA); N-(2-Hydroxyethyl)iminodiacetic acid (HIDA); Iminodiacetic acid (IDA); 1,2-Diaminopropane-N,N,N',N'-tetraacetic acid (Methyl-EDTA); Nitrillotriacetic acid (NTA); Nitrilotripropionic acid (NTP); Nitrilotris(methylenephosphoric acid), trisodium salt (NTPO); 7,19.30-Trioxa-1,4,10,13,16.22,27,33-octaazabicyclo [11,11,11]pentatriacontane, hexahydrobromide (O-Bistren); Triethylenetetramine-N,N,N',N'',N''',N''''-hexaacetic acid (TTHA); cyclohexyl TTHA; diethylenetriaminepentaacetic acid (DTPA); cyclohexyl DTPA; ethylenebis-N,N'-(2-o-hydroxyphenyl)glycine; 2-[[2-bis(carboxymethyl)amino]-5-methylphenoxy]methyl]-8-bis(carboxymethyl)amino]-quinolone; 2-[[2-[bis(carboxymethyl)amino]-5-methylphenoxy]-6-methoxy-8-[bis(carboxy-methyl)amino]quinolone; O,O'-bis(2-aminoethyl)ethyleneglycol-N,N,N',N'-tetraacetic acid; 8-hydroxyquinoline; 2-hydroxypyridine-1-oxide; salicylaldehyde isonicotinoyl hydrazine; thenoyl trifluoro acetone; dihydroxyacetate, tropolone; hydroxyethylidine-I; diphosphonic acid; dehydroacetic acid; glucoheptanoic acid; salts, esters, solvates, hydrates, derivatives, analogs, and combinations, thereof.

In some non-limiting embodiments, the one or more compounds having metal chelating moieties may be provided in the analyte indicator 106 (e.g., polymer graft or hydrogel) of the analyte sensor 100. In some non-limiting embodiments, the one or more compounds having metal chelating moieties may be provided in the analyte indicator 106 by entrapping the one or more compounds having metal chelating moieties in the analyte indicator 106. In some embodiments, the one or more compounds entrapped in the analyte indicator 106 may be immobilized in the analyte indicator 106 but not chemically attached to the analyte indicator 106. In some non-limiting aspects, the one or more compounds having metal chelating moieties may be additionally or alternatively entrapped in a hydrogel covering at least a portion of the sensor housing, and the hydrogel entrapping the one or more compounds having metal chelating moieties may be separate and distinct from the analyte indicator 106. In some non-limiting embodiments in which the analyte indicator 106 includes the one or more compounds having metal chelating moieties, the one or more compounds having metal chelating moieties may be entrapped in the analyte indicator 106 by a method including one or more of the followings steps: (i) providing the analyte indicator 106 on the outer surface of the sensor housing 102, (ii) preparing a composition including the one or more compounds having metal chelating moieties (e.g., preparing a solution of the one or more compounds having metal chelating moieties in a solvent), (iii) inserting the analyte sensor 100 into the composition for an amount of time sufficient to effect soaking of the composition into the analyte indicator 106 on the sensor housing 102, (iv) removing the analyte sensor 100 from the composition, and (v) drying the analyte sensor 100. In some aspects, the solvent may include, for example and without limitation, an alcohol (e.g., isopropanol, ethanol, or methanol), water, or a combination thereof. In some aspects, the composition may include, for example and without limitation, about 0.01 to about 25% by weight of the compounds having one or more compounds having metal chelating moieties (e.g., 0.01, 0.05, 0.1, 0.5, 1, 2, 5, 10, 15, 20, 25% by weight, or any integer or fraction thereof falling in the range between 0.01 and 25% by weight of the composition of the compounds having one or more compounds having metal chelating moieties). In some aspects, the analyte sensor 100 may remain in the composition for amount of time in a range from about 5 minutes to about 24 hours (e.g., 5, 10, 20, 30, 40, 50, or 60 minutes, or 2, 4, 6, 8, 10, 12, 14, 16, 18, 20, 22, or 24 hours, or any specific time period falling in the range between 5 minutes and 24 hours). In some aspects, the analyte sensor 100 may be air dried.

In some aspects, the one or more compounds having metal chelating moieties may be chemically attached to monomers or macromolecules forming the hydrogel.

In some aspects, the one or more compounds having metal chelating moieties may be co-polymerized as a co-monomer with an indicator monomer and one or more acrylate monomers. In some non-limiting embodiments, one or more compounds having metal chelating moieties may be provided as co-monomers of four monomers according to Formula V:

ABCD            [Formula V], wherein A is an indicator monomer, B is a methacrylate monomer, C is a polyethylene glycol monomer, and D is a metal chelating moiety monomer, wherein A is 0.001 to 10% by weight, B is 20 to 90% by weight, C is 1 to 60% by weight, and D is 0.1 to 80% by weight of the total polymer.

In some aspects, the one or more compounds having metal chelating moieties may include forming the hydrogel and then reacting the already formed hydrogel with the one or more compounds having metal chelating moieties to chemically attach the one or more compounds having metal chelating moieties to the hydrogel.

In some non-limiting embodiments, the analyte indicator 106 may contain: (i) the TFM fluorescent indicator, (ii) hydroxyethylmethacrylate (HEMA), which is a methacrylate, (iii) polyethylene glycol (PEG), and (iv) one or more compounds having metal chelating moieties. In some embodiments, the PEG may be polyethylene glycol methacrylate (PEG-methacrylate) or polyethylene glycol diacrylate (PEG-diacrylate or PEGDA). In some embodiments, i) through iv) may be provided in specific molar ratios. For example, in some non-limiting embodiments in which the analyte indicator 106 is opaque, the analyte indicator 106 may comprise 0.001 to 10% by weight, HEMA may comprise 20 to 90% by weight, PEGDA may comprise 1 to 60% by weight of the total polymer, and the one or more compounds having metal chelating moieties may comprise 0.01 to 80% percent by weight of the total polymer.

In some embodiments, the PEGDA may act as a cross-linker and create a sponge-like matrix/hydrogel. In some non-limiting embodiments, the PEG-containing graft/hydrogel may become clear if a sufficient amount of additional PEG is added to the mixture (i.e., if it is fabricated with a higher concentration of PEG), and a clear polymer graft 106 may be made from such a formulation. In some embodiments, the polymer graft may be synthesized using conventional free radical polymerization.

Figure 4:
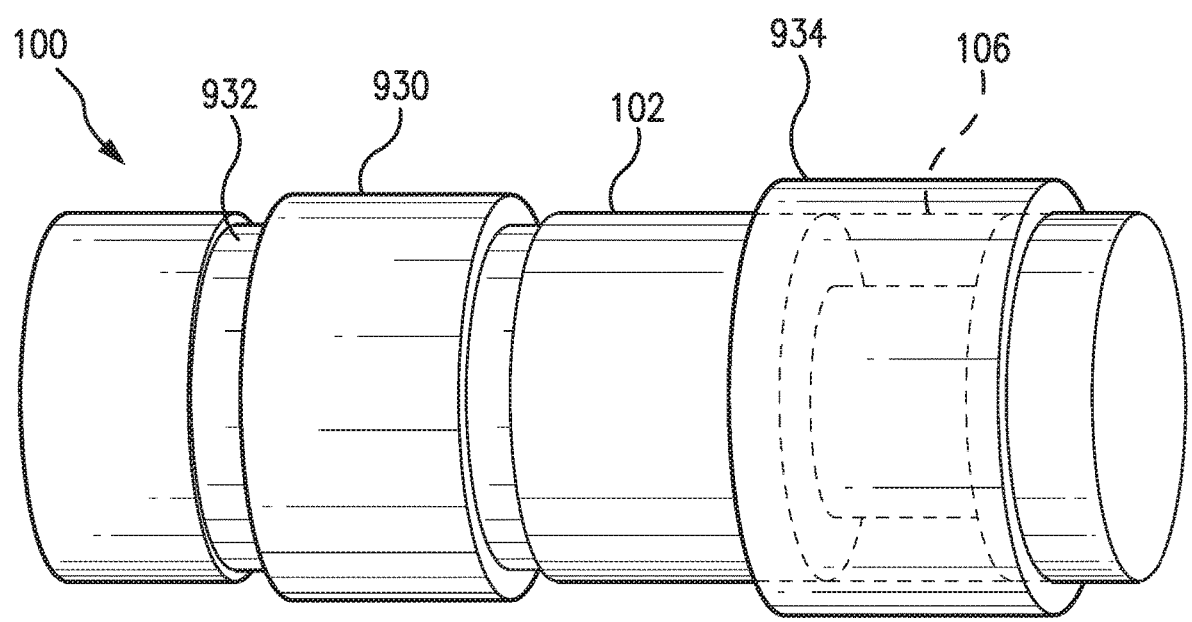
FIG. 4 illustrates a perspective view of a sensor embodying aspects of the present invention.

FIG. 4 illustrates a non-limiting embodiment of a sensor 100 embodying aspects of the present invention that may be used in the sensor system illustrated in FIG. 1. In some non-limiting embodiments, as shown in FIG. 4, the sensor 100 may include one or more of a first material 934 and a second material 930. In some embodiments, the first material 934 may cover at least a portion of the analyte indicator 106. In some embodiments, the first material 934 may additionally cover at least a portion of the sensor housing 102, but this is not required. In some embodiments, the second material 930 may cover at least a portion of the sensor housing 102. In some embodiments, the second material 930 may be separate and distinct from the analyte indicator 106. In some embodiments, the second material 934 does not cover any portion of the analyte indicator 106. In some non-limiting embodiments, as shown in FIG. 4, the sensor housing 102 may include a groove 932, and the second material 934 may be positioned in the groove 932. In some embodiments, the edges of the groove 932 may assist in holding the second material 934 in place on the sensor housing 102. In some embodiments, one or more of the first and second materials 930 and 934 may be a polymer matrix, polymer graft, and/or hydrogel. However, the first and second materials 930 and 934 are not required, and, in some embodiments, the sensor 100 may not include one or more of the first material 934 and the second material 930.

In some non-limiting embodiments, in addition to (or as an alternative to) the analyte indicator 106 including the one or more compounds having metal chelating moieties, one or more of the first and second materials 934 and 930 may include the one or more compounds having metal chelating moieties. In some embodiments, the one or more compounds having metal chelating moieties included in one or more of the first and second materials 934 and 930 may be entrapped in one or more of the first and second materials 934 and 930 or chemically attached to one or more of the first and second materials 934 and 930. In some embodiments, the second material 930 may additionally or alternatively be a drug eluting polymer matrix.

In some embodiments, an additive-containing sensor (e.g., an implanted sensor 100 including an additive-containing analyte indicator 106) may have improved performance over a sensor that does not include an additive. For instance, in some non-limiting embodiments, the additive may improve the longevity and/or functionality of the sensor 100.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although in some embodiments, the analyte sensor 100 may be an optical sensor, this is not required, and, in one or more alternative embodiments, the analyte sensor may be a different type of analyte sensor, such as, for example, an electrochemical sensor, a diffusion sensor, or a pressure sensor. Also, although in some embodiments, the analyte sensor 100 may be an implantable sensor, this is not required, and, in some alternative embodiments, the analyte sensor may be a transcutaneous sensor having a wired connection to an external transceiver. For example, in some alternative embodiments, the analyte sensor 100 may be located in or on a transcutaneous needle (e.g., at the tip thereof). In these embodiments, instead of wirelessly communication using an antenna (e.g., inductive element 114), the analyte sensor may communicate with the external transceiver using one or more wires connected between the external transceiver and a transceiver transcutaneous needle including the analyte sensor. For another example, in some alternative embodiments, the analyte sensor may be located in a catheter (e.g., for intravenous blood glucose monitoring) and may communicate (wirelessly or using wires) with an external transceiver.

What is claimed is:

1. A sensor for measurement of an analyte in a medium within a living animal, the sensor comprising:
    a sensor housing;
    an analyte indicator covering at least a portion of an outer surface of the sensor housing, wherein the analyte indicator comprises fluorescent indicator molecules comprising a boronate group; and
    one or more compounds having metal chelating moieties on an outer surface of the sensor housing.

2. The sensor of claim 1, wherein the sensor is implantable within a living animal.

3. The sensor of claim 1, wherein the analyte indicator further includes the one or more compounds having metal chelating moieties.

4. The sensor of claim 3, wherein the one or more compounds having metal chelating moieties are entrapped in the analyte indicator.

5. The sensor of claim 3, wherein the one or more compounds having metal chelating moieties are chemically attached to the analyte indicator.

6. The sensor of claim 5, wherein the one or more compounds having metal chelating moieties are co-polymerized with the analyte indicator.

7. The sensor of claim 1, wherein the analyte indicator is a hydrogel.

8. The sensor of claim 7, wherein the one or more compounds having metal chelating moieties are entrapped in the hydrogel.

9. The sensor of claim 7, wherein the one or more compounds having metal chelating moieties are chemically attached to monomers forming the hydrogel.

10. The sensor of claim 9, wherein the one or more compounds having metal chelating moieties are co-polymerized with monomers forming the hydrogel.

11. The sensor of claim 7, wherein the one or more compounds having metal chelating moieties are chemically attached to an indicator macromolecule forming the hydrogel.

12. The sensor of claim 1, wherein one or more compounds having metal chelating moieties are provided as a polymer of four monomers according to formula V: ABCD, wherein A is an indicator monomer, B is a methacrylate monomer, C is a polyethylene glycol monomer, and D is a metal chelating moiety monomer.

13. The sensor of claim 12, wherein A is present up to 10% by weight, B is 1 to 99% by weight, C is 1 to 99% by weight, and D is 0.1 to 99% by weight of the total polymer.

14. The sensor of claim 12, wherein A is 0.001 to 10% by weight, B is 20 to 90% by weight, C is 1 to 60% by weight, and D is 0.1 to 80% by weight of the total polymer.

15. The sensor of claim 1, wherein the one or more compounds having metal chelating moieties interact or react with a degradative species without compromising signal integrity or performance of the sensor device.

16. The sensor of claim 15, wherein the degradative species is hydrogen peroxide, a reactive oxygen species, a reactive nitrogen species, a free radical, an enzyme, or a metal ion.

17. The sensor of claim 15, wherein the degradative species is a metal ion.

18. The sensor of claim 1, wherein the one or more compounds having metal chelating moieties reduce a degradation rate of the analyte indicator.

19. The sensor of claim 15, wherein the one or more compounds having metal chelating moieties bind to the degradative species.

20. The sensor of claim 15, wherein the one or more compounds having metal chelating moieties sequester the degradative species so as to reduce, and/or prevent degradation of the analyte indicator by the degradative species.

21. The sensor of claim 1, wherein the one or more compounds having metal chelating moieties are selected from ethylenediaminetetraacetic acid (EDTA); an EDTA free acid, an EDTA salt, an EDTA ester, an EDTA solvate, an EDTA hydrate; cyclohexyl EDTA; cyclohexyl EDTA monoanhydride (CDTAMA); trans-1,2-Diaminocyclohexane-N,N,N',N'-tetraaceticacid, monohydrate (CyDTA); N,N-Bis(2-hydroxyethyl)glycine (DHEG); 1,3-Diamino-2-hydroxypropane-N,N,N',N'-tetraacetic acid (DTPA-OH); Ethylenediamine-N,N'-diacetic acid (EDDA); Ethylenediamine-N,N'-dipropionic acid dihydrochloride (EDDP); Ethylenediamine-N,N'-bis(methylenephosphonic acid), hemihydrate (EDDPO); N-(2-Hydroxyethyl)ethylenediamine-N,N',N'-triacetic acid (EDTA-OH); Ethylenediamine-N,N,N',N'-tetrakis(methylenephosponic acid) (EDTPO); 0,0'-bis(2-aminoethyl)ethyleneglycol-N,N,N',N'-tetraacetic acid (EGTA); N,N-bis(2-hydroxybenzyl)ethylenediamine-N,N-diacetic acid (HBED); 1,6-Hexamethylenediamine-N,N,N',N'-tetraacetic acid (HDTA); N-(2-Hydroxyethyl)iminodiacetic acid (HIDA); Iminodiacetic acid (IDA); 1,2-Diaminopropane-N,N,N',N'-tetraacetic acid (Methyl-EDTA); Nitrillotriacetic acid (NTA); Nitrilotripropionic acid (NTP); Nitrilotris(methylenephosphoric acid), trisodium salt (NTPO); 7,19.30-Trioxa-1,4,10,13,16.22,27,33-octaazabicyclo [11,11,11]pentatriacontane, hexahydrobromide (0-Bistren); Triethylenetetramine-N,N,N',N'',N''',N'''-hexaacetic acid (TTHA); cyclohexyl TTHA; diethylenetriaminepentaacetic acid (DTPA); cyclohexyl DTPA; ethylenebis-N,N'-(2-o-hydroxyphenyl)glycine; 2-[[2-bis(carboxymethyl)amino]-5-methylphenoxy]methyl]-8-bis(carboxymethyl)amino]-quinolone; 2-[[2-[bis(carboxymethyl)amino]-5-methylphenoxy]-6-methoxy-8-[bis(carboxy-methyl)amino]quinolone; 0,0'-bis(2-aminoethyl)ethyleneglycol-N,N,N',N'-tetraacetic acid; 8-hydroxyquinoline; 2-hydroxypyridine-1-oxide; salicylaldehyde isonicotinoyl hydrazine; thenoyl trifluoro acetone; dihydroxyacetate, tropolone; hydroxyethylidine-I; diphosphonic acid; dehydroacetic acid; glucoheptanoic acid; salts, esters, solvates, hydrates, and combinations thereof.

22. The sensor of claim 1, wherein the sensor further comprises at least one drug eluting polymer matrix that covers at least a portion of the sensor housing.

23. The sensor of claim 1, further comprising a material including one or more compounds having metal chelating moieties.

24. The sensor of claim 23, wherein the material covers at least a portion of the analyte indicator.

25. The sensor of claim 23, wherein the material covers at least a portion of the sensor housing.

26. A method of fabricating a sensor for measurement of an analyte in a medium within a living animal, the method comprising:
inserting the sensor into a composition for an amount of time sufficient to effect soaking of the composition into an analyte indicator, wherein the sensor includes a sensor housing and the analyte indicator that covers at least a portion of an outer surface of the sensor housing, and the composition comprises one or more compounds having metal chelating moieties; and removing the sensor from the composition to obtain the sensor of claim 1.

27. The sensor of claim 1, wherein the sensor housing encases one or more photodetectors sensitive to fluorescent light emitted by the fluorescent indicator molecules within the sensor housing.

28. The sensor of claim 1, wherein the one or more compounds having metal chelating moieties are selected from O,O'-bis(2-aminoethyl)ethyleneglycol-N,N,N',N'-tetraacetic acid (EGTA); N,N-bis(2-hydroxybenzyl)ethylenediamine-N,N-diacetic acid (HBED); 1,6-Hexamethylenediamine-N,N,N',N'-tetraacetic acid (HDTA); Nitrilotripropionic acid (NTP); Nitrilotris(methylenephosphoric acid), trisodium salt (NTPO); 7,19,30-Trioxa-1,4,10,13,16,22,27,33-octaazabicyclo pentatriacontane, hexahydrobromide; Triethylenetetramine-N,N,N',N'',N''',N'''-hexaacetic acid (TTHA); cyclohexyl TTHA; diethylenetriaminepentaacetic acid (DTPA); cyclohexyl DTPA; ethylenebis-N,N'-(2-o-hydroxyphenyl)glycine; 2-[[2-bis(carboxymethyl)amino]-5-methylphenoxy] methyl]-8-bis(carboxymethyl)amino]— quinolone; 2-[[2-[bis(carboxymethyl)amino]-5-methylphenoxy]-6-methoxy-8-[bis(carboxy-methyl)amino]quinolone; 0,0'-bis(2-aminoethyl)ethyleneglycol-N,N,N',N'-tetraacetic acid; 8-hydroxyquinoline; 2-hydroxypyridine-1-oxide; salicylaldehyde isonicotinoyl hydrazine; thenoyl trifluoro acetone; dihydroxyacetate, tropolone; hydroxyethylidine-I; diphosphonic acid; dehydroacetic acid; glucoheptanoic acid; salts, esters, solvates, hydrates, and combinations thereof.

\* \* \* \* \*